US008557733B2

(12) United States Patent
Skulachev et al.

(10) Patent No.: US 8,557,733 B2
(45) Date of Patent: Oct. 15, 2013

(54) COMPOSITION FOR REGENERATING AND STIMULATING GROWTH OF PLANTS AND FOR ADAPTING PLANTS TO DIFFERENT STRESS FACTORS

(75) Inventors: Vladimir Petrovich Skulachev, Moscow (RU); Maxim Vladimirovich Skulachev, Moscow (RU)

(73) Assignee: Mitotech S.A., Luxembourg (LU)

( * ) Notice: Subject to any disclaimer, the term of this patent is extended or adjusted under 35 U.S.C. 154(b) by 576 days.

(21) Appl. No.: 12/445,902

(22) PCT Filed: Oct. 20, 2006

(86) PCT No.: PCT/RU2006/000547
§ 371 (c)(1),
(2), (4) Date: Nov. 30, 2010

(87) PCT Pub. No.: WO2008/048135
PCT Pub. Date: Apr. 24, 2008

(65) Prior Publication Data
US 2011/0077159 A1      Mar. 31, 2011

(51) Int. Cl.
*A01N 3/02* (2006.01)
*A01N 57/18* (2006.01)
(52) U.S. Cl.
USPC .......................................... 504/114; 504/207
(58) Field of Classification Search
None
See application file for complete search history.

(56) References Cited

U.S. PATENT DOCUMENTS

| | | | |
|---|---|---|---|
| 4,066,435 A | 1/1978 | Howe | |
| 4,173,462 A | 11/1979 | Brown | |
| 5,538,974 A | 7/1996 | Ogawa et al. | |
| 6,331,532 B1 * | 12/2001 | Murphy et al. | 514/100 |
| 7,109,189 B2 | 9/2006 | Murphy et al. | |
| 2005/0065099 A1 | 3/2005 | Walkinshaw et al. | |
| 2007/0259908 A1 | 11/2007 | Fujii et al. | |
| 2007/0270381 A1 | 11/2007 | Murphy et al. | |
| 2008/0275005 A1 | 11/2008 | Murphy et al. | |

FOREIGN PATENT DOCUMENTS

| | | |
|---|---|---|
| EP | 1047701 B1 | 5/2005 |
| EP | 1534720 A1 | 6/2005 |
| EP | 1321138 B1 | 4/2006 |
| RU | 2318500 C2 | 3/2008 |
| SU | 384200 | 3/1974 |
| WO | 99/26582 A2 | 6/1999 |
| WO | 2004/014927 A1 | 2/2004 |
| WO | 2006/005759 A2 | 1/2006 |
| WO | 2007/046729 A1 | 4/2007 |
| WO | 2008/048134 A1 | 4/2008 |
| WO | 2009/005386 A1 | 1/2009 |
| WO | 2009/158348 A1 | 12/2009 |

OTHER PUBLICATIONS

Bakeeva et al. (2008) "Mitochondria-targeted plastoquinone derivatives as tools to interrupt execution of the aging program. 2. Treatment of some ROS- and Age-related diseases (heart arrhythmia, heart infarctions, kidney ischemia, and stroke)," Biochemistry (Moscow), 73(12):1288-1299 and 1 figure.
Clem et al. (2008) "Small-molecule inhibition of 6-phosphofructo-2-kinase activity suppresses glycolytic flux and tumor growth," Mol. Canc. Ther. 7(1):110-120.
Goldstein (2002) "Reactive oxygen species as essential components of ambient air," Biochemistry (Mosc.) 67:161-170.
Green (1974) "The electromechanochemical model for energy coupling in mitochondria," Biochimica et Biophysica Acta, 346:27-78.
Kirste et al. (1995) "Continuous-wave electron spin resonance studies of porphyrin and porphyrin-quinone triplet states," J. Chem. Soc. Perkin Trans. 2:2147-2152.
Murphy et al. (2007) Targeting antioxidants to mitochondria by conjugation to lipophilic cations. Annu. Rev. Pharmacol. Toxicol., 47:629-656.
Plotnikov et al. (2008) "Interrelations of Mitochondrial Fragmentation and Cell Death Under Ischemia/Reoxygenation and UV-Irradiation: Protective Effects of SkQ1, Lithium Ions and Insulin," FEBS Letters, 582:3117-3124.
Plotnikov et al. (2010) "New-generation Skulachev ions exhibiting nephroprotective and neuroprotective properties." Biochemistry (Mosc.), 75(2):145-150.
Skulachev et al. (2005) "Aging as mitochondria-mediated atavistic program. Can aging be switched off?" Ann. N.Y. Acad. Sci., 1057:145-164.
Skulachev et al. (2009) "An attempt to prevent senescence: a mitochondrial approach," Biochimica et Biophysica Acta., 1787:437-461.
Smith et al. (2008) "Mitochondria-targeted antioxidants in the treatment of disease,"Ann. N.Y. Acad. Sci., 1147:105-111.
Snow et al. (2010) "A double-blind, placebo-controlled study to assess the mitochondria-targeted antioxidant MitoQ as a disease-modifying therapy in Parkinson's disease," Mov. Disord. 25(11):1670-1674.
Stefanova et al. (2010) "Behavioral effects induced by mitochondria-targeted antioxidant SkQ1 in Wistar and senescence-accelerated OXYS rats," J. Alzheimer's Dis. 21:479-491.
Tauskela (2007) "MitoQ—a mitochondria-targeted antioxidant," IDrugs, 10:399-412.
Triet et al. (1993) "Anxiogenic stimuli in the elevated plus-maze," Pharmacol. Biochem. & Behav. 44:463-469.
International Search Report and Written Opinion of the International Searching Authority, PCT/RU2009/000295, Feb. 25, 2010, 7 pages.
International Search Report and Written Opinion, PCT/RU2009/000621, dated Aug. 12, 2010 (12 pages).
International Search Report and Written Opinion, PCT/RU2006/000394, dated Nov. 2, 2006 (6 pages).

(Continued)

Primary Examiner — Alton Pryor
(74) Attorney, Agent, or Firm — Furman Gregory

(57) ABSTRACT

The present invention relates to biotechnology. The invention can be used for stimulation of regeneration of plants from tissues and undifferentiated cells cultivated under artificial conditions. The present invention can also be applied in agriculture for acceleration of germination of seeds, increase in germination of aged, long-stored seeds as well as for increase of resistance of plants to biotic and abiotic stresses.

13 Claims, 8 Drawing Sheets

(56) References Cited

OTHER PUBLICATIONS

Adlam et al. (2005) "Targeting an antioxidant to mitochondria decreases cardiac ischemia-reperfusion injury," FASEB J., 19:1088-1095.
Agapova et al. (2008) "Mitochondria-Targeted Plastoquinone Derivatives as Tools to Interrupt Execution of the Aging Program. 3. Inhibitory Effect of SkQ1 on Tumor Development From p53-Deficient Cells," Biochem. (Mosc)., 73 (12):1300-1316 (+ 3 fig. pages).
Anisimov (2007) "Molecular and Physiological Mechanisms of Aging," Antioksidanty, Nov. 27, 2007, [on line] http://imquest.alfaspace.net/BOOK/MFMA/mfma_3_9_2.htm?embedded=yes translated from Russian to English.
Antonenko et al. (2008) "Mitochondria-Targeted Plastoquinone Derivatives as Tools to Interrupt Execution of the Aging Program. 1. Cationic Plastoquinone Derivatives: Sythesis and in vitro Studies," Biochemistry, 73(12)1273-1287.
Antonenko et al. (2008) "Protective effects of mitochondria-targeted antioxidant SkQ in aqueous and lipid membrane environments," J. Membr. Biol., 222:141-149.
Becker (2004) "New concepts in reactive oxygen species and cardiovascular reperfusion physiology" Cardiovascular Research, 61:461-470.
Berge et al. (1977) "Pharmaceutical Salts," J. Pharma. Sci., 66(1):1-19.
Blaikie et al. (2006) "Targeting Dinitrophenol to Mitochondria: Limitations to the Development of a Self-limiting Mitochondrial Protonophore," Biosci. Rep., 26:231-243.
Brand et al. (1992) "The mechanism of the increase in mitochondrial proton permeability induced by thyroid hormones," Eur. J. Biochem. 206:775-781.
Doughan et al. (2007) "Original Research Communication: Mitochondrial Redox Cycling of Mitoquinone Leads to superoxide Production and Cellular Apoptosis," Antioxid. & Redox Signal., 9(11):1825-1836.
Kasahara, et al. (2005) "Manganese Superoxide Dismutase protects against oxidation-induced apoptosis in mouse retinal pigment epithelium: implications for age-related macular degeneration," Author Manuscript, NIH Public Access PMC Nov. 1, 2005 : 1-18, Invest. Ophthalmol. Vis. Sci., 46(9):3426-3434.
Green et al. (2004) "Prevention of Mitochondrial Oxidative Damage as a Therapeutic Strategy in Diabetes," Diabetes, 53(1):S110-S118.
Hansford et al. (1997) "Dependence of H2O2 formation by rat heart mitochondria on substrate availability and donor age," J. Bioenerg. Biomem. 29(1):89-95.
Havens et al. (2006) "Regulation of Late G1/S Phase Transition and APCCdh1 by Reactive Oxygen Species," Mol. Cell. Biol., 26(12):4701-4711.
Holloszy (1998) "Longevity of exercising male rats: effect of an antioxidant supplemented diet," Mechanisms of Ageing and Development, 100:211-219.
King et al. (2004) "Mitochondria-derived reactive oxygen species mediate blue light-induced death of retinal pigment epithelial cells," Photochem. and Photobiol., 79(5):470-475.
Kirschner et al. (1994) "Role of iron and oxygen-derived free radicals in ischemia-reperfusion injury" J. Am. Coll. Surg., 179:103-117.
Li et al. (2000) "Skeletal muscle respiratory uncoupling prevents diet-induced obesity and insulin resistance in mice," Nat. Med. 6(10):1115-1120.
Liu et al. (1993) "Age-associated changes in superoxide dismutase activity, thiobarbituric acid reactivity and reduced glutathione level in the brain and liver in senescence accelerated mice (SAM): a comparison with ddY mice," Mech. Ageing & Dev., 71:23-30.
Longo et al. (2005) "Programmed and altruistic ageing," Nature Reviews Genetics, 6:866-872.
Lou et al. (2007) "Mitochondrial Uncouplers With an Extraordinary Dynamic Range," Biochem. J., 407:129-140.
Mecocci et al. (2000) "Plasma antioxidants and longevity: a study on healthy centenarians," Free Radical Biology and Medicine, 28(8):1243-1248.

Neroev et al. (2008) Mitochondria-Targeted Plastoquinone Derivatives as Tools to Interrupt Execution of the Aging Program. 4. Age-Related Eye Disease. SkQ1 Returns Vision to Blind Animals, Biochemistry (Mosc.), 73 (12):1317-1328.
Orr et al. (2003) "Effects of overexpression of copper-zinc and manganese superoxide dismutases, catalase, and thioredoxin reductase genes on longevity in *Drosophila melanogaster*," J. Biol. Chem., 278(29):26418-26422.
Papp et al. (1999) "Glutathione status in retinopathy of prematurity," Free Radic. Biol. & Med., 27(7-8):738-743.
Petrosillo et al. (2005) "Mitochondrial dysfunction associated with cardiac ischemia/reperfusion can be attenuated by oxygen tension control. Role of oxygen-free radicals and cardiolipin," Biochimica et Biophysica Acta, 1710:78-86.
Petrosillo et al. (2006) "Protective effect of melatonin against mitochondrial dysfunction associated with cardiac ischemia-reperfusion: role of cardiolipin," FASEB J., 20:269-276.
Popova et al. (2006) "MitoQ induced miofibroblast differentiation of human fibroblasts," Biochimica et Biophysica Acta, S:433-434.
Popova et al. (2010) "Scavenging of Reactive Oxygen Species in Mitochondria Induces Myofibroblast Differentiation," Antiox. & Redox. Signal., 13(9):1297-1307.
Pozniakovsky et al. (2005) "Role of mitochondria in the pheromone- and amiodarone-induced programmed death of yeast," J. Cell Biol., 168(2):257-69.
Reddy (2006) "Mitochondrial oxidative damage in aging and Alzheimer's disease: implications for mitochondrially targeted antioxidant therapeutics," J. Biomedicine and Biotech., Art.ID 31372:1-13.
Reliene et al. (2007) "Antioxidants suppress lymphoma and increase longevity in atm-deficient mice," J. Nutrition, 137:229S-232S.
Riess et al. (2004) "Reduced reactive O2 species formation and preserved mitochondrial NADH and [Ca2+] levels during short-term 17° C. ischemia in intact hearts," Cardiovascular Research, 61:580-590.
Skulachev (2007) "A Biochemical Approach to the Problem of Aging: 'Megaproject' on Membrane-Penetrating Ions. The First Results and Prospects," Biochem. (Moscow), 72(12):1385-1396.
Sheu et al. (2006) "Targeting antioxidants to mitochondria: a new therapeutic direction," Biochimica et Biophysica Acta, 1762:256-265.
Sidorova et al. (2004) "Transcriptional activation of cytochrome P450 1A1 with alpha-tocopherol," Bull Exp. Bio. Med., 138(3):233-236.
Skulachev (2005) "Critical Review: How to Clean the Dirtiest Place in the Cell: Cationic Antioxidants as Intramitochondrial ROS Scavengers," IUBMB Life, 57(4/5):305-310.
Skulachev (2003) "Aging and the programmed death phenomena," Topics in Current Genetics, vol. 3, Nystrom and Osiewacz, Eds., Model systems in Aging, Springer-Verlag Berlin Heidelberg 191-238.
Sundaresan et al. (1995) "Requirement for Generation of H2O2 for Platelet-Derived Growth Factor Signal Transduction," Science, 270:296-299.
Starkov et al. (1997) "6-ketocholestanol is a recoupler for mitochondria, chromatophores and cytochrome oxidase proteoliposomes," Biochim. Biophys. Acta. 1318:159-172.
Tompkins et al. (2006) "Mitochondrial dysfunction in cardiac ischemia-reperfusion injury: ROS from complex I, without inhibition," Biochim. Biophys. Acta. 1762:223-231.
Yildirim et al. (2005) "Role of oxidative stress enzymes in open-angle glaucoma," Eye, 19:580-583.
Zweier et al. (1987) "Direct measurement of free radical generation following reperfusion of ischemic myocardium," PNAS USA, 84:1404-1407.
International Search Report dated Dec. 20, 2007 and International Preliminary Report on Patentability dated Nov. 10, 2009, PCT/RU2007/000171 (16 pages).
International Search Report and Written Opinion of the International Searching Authority, PCT/RU2007/000355, Mar. 27, 2008 (10 pages).

(56) References Cited

OTHER PUBLICATIONS

PCT International Search Report mailed Nov. 1, 2007 and International Preliminary Report on Patentability issued Aug. 4, 2009 for PCT Application No. PCT/RU2007/000043, 9 pages.
International Search Report and Written Opinion, PCT/RU2006/000547, dated Jul. 5, 2007 (7 pages).
PCT International Search Report and Written Opinion of the International Searching Authority for PCT Application No. PCT/RU2006/000546, mailed Jul. 5, 2007, 14 pages.
International Search Report and Written Opinion of the International Searching Authority, PCT/RU2007/000044, Nov. 1, 2007 (9 Pages).
International Search Report, PCT/RU2008/000706, Aug. 13, 2009 (3 pages).
Ahuja and Libby (eds.) 1993. Clonal Forestry I: Genetics and Biotechnology. Springer-Verlag. Berlin.
von Aderkas, et al., "Influencing Miocropropagation and Somatic Embryogenesis in Mature Trees by Manipulation of Phase Change, Stress and Culture Environment," Tree Physiol., 20:921-928 (2000).
Merkle, et al., "Forest Tree Biotechnology," Curr. Opin. Biotechnol., 11:298-302 (2000).
Tisserat, et al., "Clonal Propagation of Orchids," Methods Mol. Biol., 111:127-134 (1999).
Karp, "Somaclonal Variation as a Tool for Crop Improvement," Euphytica, 85:295-302 (1995).
Ahuja and Libby (eds.) 1993. Clonal Forestry II: Conservation and Application. Springer-Verlag. Berlin.
Loyola-Vargas, et al. (eds.) 2005. Methods in Molecular Biology, Plant Cell Culture Protocols, Second Edition, Humana Press, NJ, 416 pages.
Laimer, et al. (eds.), Plant Tissue Culture: 100 Years Since Gottlieb Haberlandt, Springer, Wien New York, 2003, 260 pages.
Yuqiang, et al., "Production and Characterization of Somatic Hybrids Between Upland Cotton (*Gossypium hirsutum*) and Wild Cotton (*G. klotzschianum* Anderss) via Electrofusion," Theor. Appl. Genet., 109:472-479 (2004).
Liu, et al., Efficient *Agrobacterium tumefaciens*-Mediated Transformation of Soybeans Using an Embryonic Tip Regeneration System, Planta, 219:1042-1049 (2004).
Vasil, et al., Histology of Somatic Embryogenesis in Cultured Immature Embryos of Maize (*Zea mays* L.), Protoplasma, 127:1-8 (1985).
Sharma, et al., Research Paper: Mature Embryo Axis-Based High Frequency Somatic Embryogenesis and Plant Regeneration From Multiple Cultivars of Barley (*Hordeum vulgare* L.), J. Exp. Bot., 56(417):1913-1922 (2005).
Dijak, et al., "Stimulation of Direct Embryogenesis From Mesophyll Protoplasts of *Medicago sativa*," Plant Cell Rep., 5:468-470 (1986).
Honda, et al., "Large-Scale Plant Micropropagation," Adv. Biochem. Eng./Biotechnol., 72:157-182, Springer-Verlag, Berlin (2001).
Dias, et al., Role of physiological factors in increase of efficiency of plant regeneration from cultivated maize tissues, Biotechnology (in Russian, abstract translation provided), No. 11-12: 32-36 (1997).
Songstad, et al., "Effect of 1-Aminocyclopropane-1-Carboxylic Acid, Silver Nitrate and Norbornadiene on Plant Regeneration From Maize Callus Cultures," Plant Cell Rep., 7:262-265 (1988).
Vain, et al., "Role of Ethylene in Embryogenic Callus Initiation and Regeneration in *Zea mays* L.," J. Plant Physiol., 135:537-540 (1989).
Shayakhmetov, et al., "Somatic Embryogenesis in Wheat Cell Suspension Cultures in the Presence of Abscisic Acid," Russian Journal of Plant Physiology 43(1):88-90 (1996), translated from Fiziologiya Rastenii, 43(1):101-103 (1996).
Brown, et al., "Control of Embryogenesis and Organogenesis in Immature Wheat Embryo Callus Using Increased Medium Osmolarity and Abscisic Acid," J. Plant Physiol., 133:727-733 (1989).
Carman, "Improved Somatic Embryogenesis in Wheat by Partial Simulation of the in-Ovulo Oxygen, Growth-Regulators and Desiccation Environments," Planta, 175:417-424 (1988).
Morocz, et al., "An Improved System to Obtain Fertile Regenerants Via Maize Protoplasts Isolated From a Highly Embryogenic Suspension Culture," Theor. Appl. Genet., 80:721-726 (1990).
Kamo, et al., "Regeneration of *Zea mays* L. From Embryonic Callus," Bot. Gaz., 146(3):327-334 (1985).
Dolgikh, et al., "Hormonal Regulation of Somatic Embryogenesis on Maize," in Phytohormones in Plant Biotechnology and Agriculture, Proceedings of NATO-Russia International Workshop, Kluwer Academic Publishers, pp. 243-247 (2003).
Armstrong, et al., "Improved Tissue Culture Response of an Elite Maize Inbred Through Backcross Breeding, and Identification of Chromosomal Regions Important for Regeneration by RFLP Analysis," Theor. Appl. Genet., 84:755-762 (1992).
Salmenkallio, et al., "Amino Acid and Peptide Uptake in the Scutella of Germinating Grains of Barley, Wheat, Rice, and Maize," Plant Physiol., 89:1285-1291 (1989).
Duncan, et al., "The Production of Callus Capable of Plant Regeneration From Immature Embryos of Numerous *Zea mays* Genotypes," Planta, 165:322-332 (1985).
Pavlova, et al., "Biological Activity of a Synthetic Pentasaccharide Fragment of Xyloglucan," Plant Sci. 85:131-134 (1992).
Hoisington, et al., "Towards the Production of Transgenic Tropical Maize Germplasm With Enhanced Insect Resistance," Curr. Issues Plant Molec. and Cell. Biol. (Terzi, et al. Eds.), Kluwer Acad. Pubs., Netherlands, pp. 327-331 (1995).
Goldsworthy, "The Electric Compass of Plants," New Sci., No. 1:22-23 (1986).
Kitlaev et al., Physiological Action of Electric Current on Maize Cell Culture in Vitro, Doklady Akademii Nauk, 335(3): 393-395 (1994) (in Russian).
Rathore, et al., "Electrical Control of Shoot Regeneration in Plant Tissue Culture," Biotechnol., 3:1107-1109 (1985).
Wang, et al., "Effect Stimulation With Weak Electric Currents on in Vitro Culture of Cabbage," Acta Bot. Sinica, 35 (Suppl.): 66-70 (1993).
International Search Report and Written Opinion of the International Searching Authority, PCT/RU2006/000547, Jul. 5, 2007 (8 pages).
PubChem compound CID 388445; Mar. 26, 2005 [retrieved from http://pubchem.ncbi.nlm.nih.gov/summary/summary.cgi?cid=38845&loc=ec_rcs on Jul. 31, 2012] whole doc (4 pages).
International Search Report and Written Opinion of the International Searching Authority, PCT/US12/40711, Aug. 20, 2012 (9 pages).

* cited by examiner

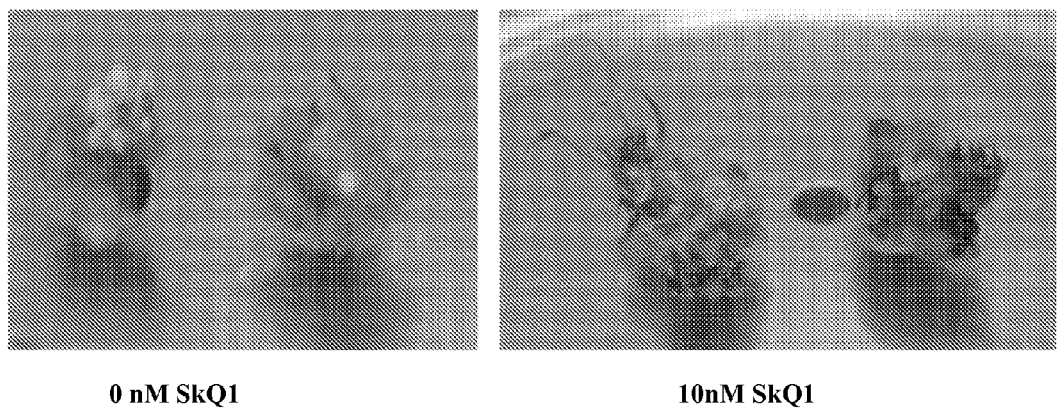
Fig. 1. SkQ1 stimulates shoot formation from undifferentiated tissue of sugar cane.

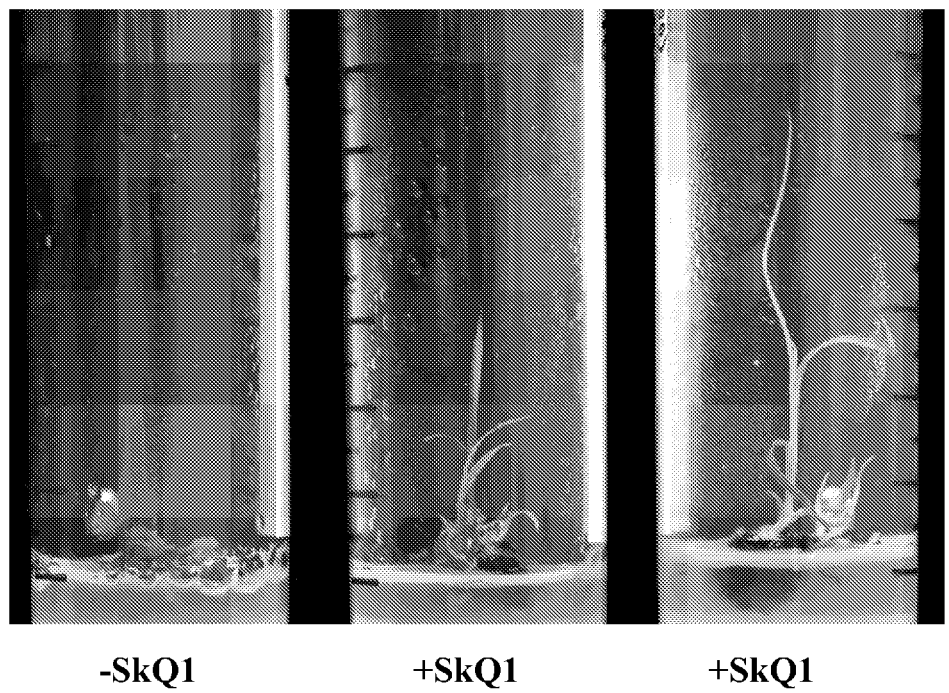
Fig. 2. Development of sugar cane shoots at regeneration medium after 10 nM SkQ1-induced shoot formation.

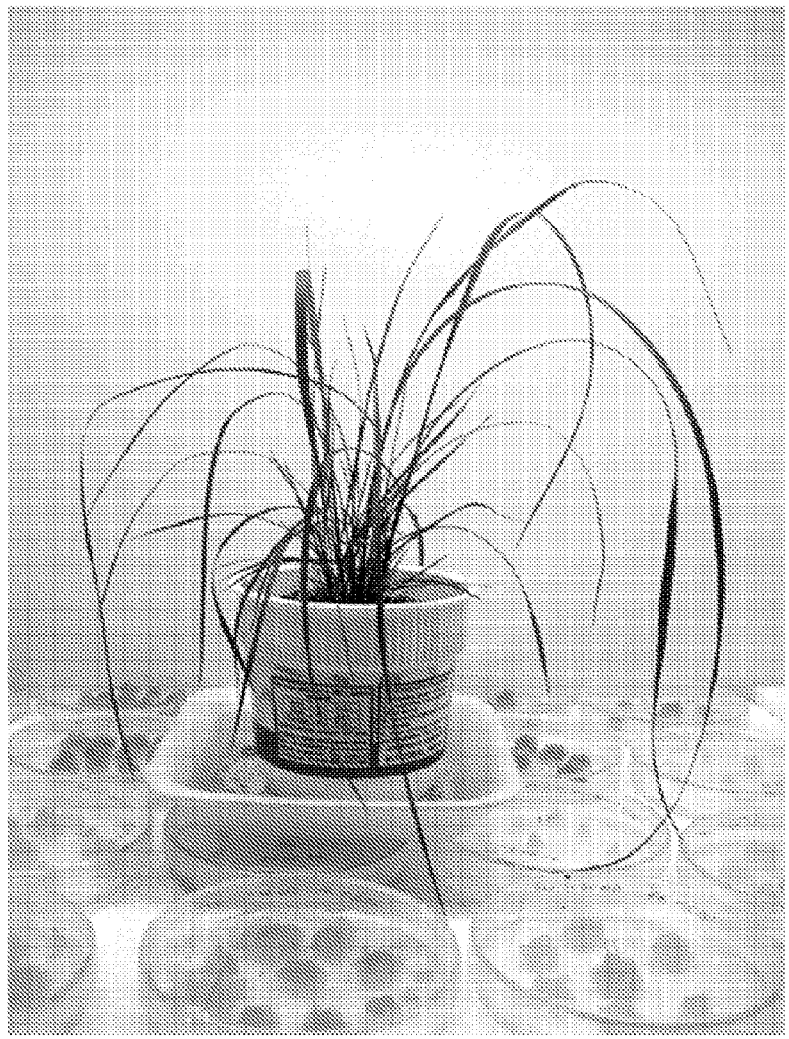
Fig. 3. A sugar cane plant produced from callus by 10 nM SkQ1-induced stimulation of regeneration.

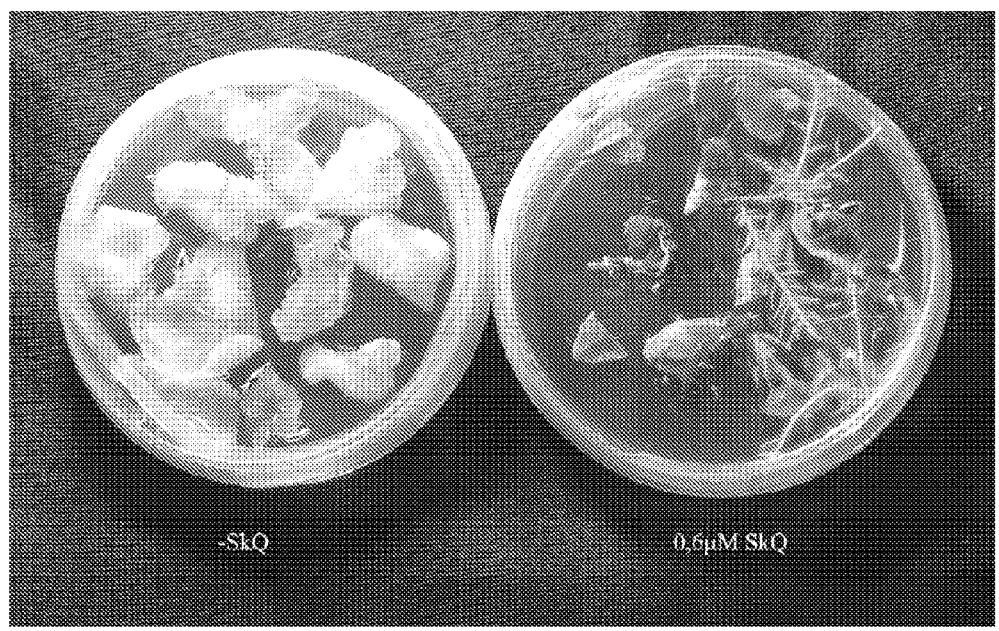
Fig. 4. SkQ1 stimulates root formation from tobacco undifferentiated tissue.

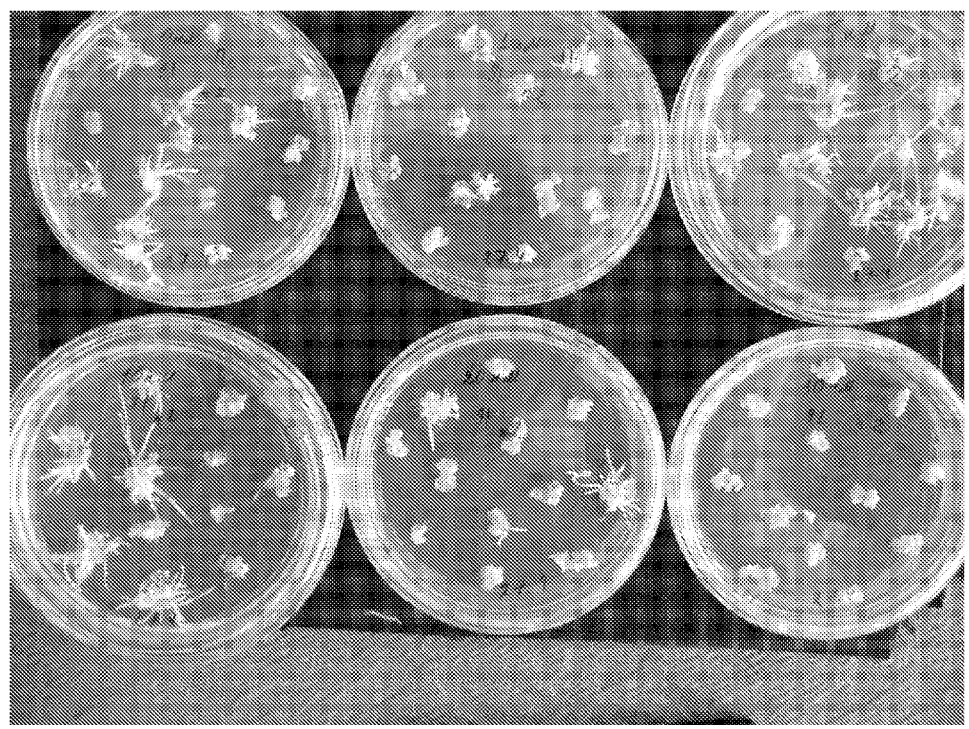
Fig. 5. Effect of different SkQ1 concentrations on formation of shoots and roots from maize calli.

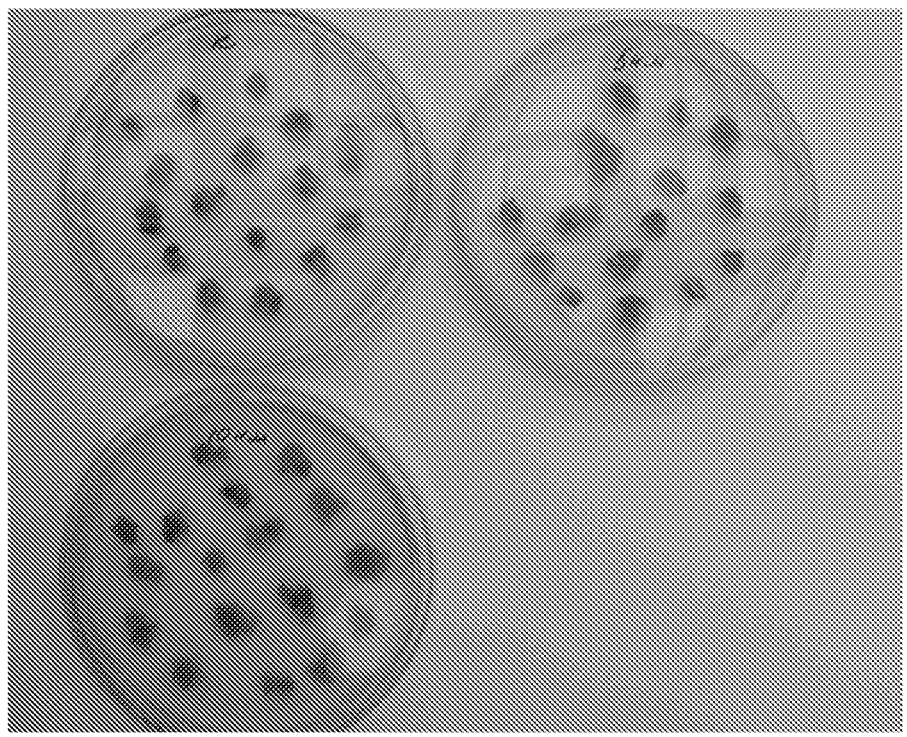
Fig. 6. Effect of SkQ1 on formation of embryogenic callus in lucerne.

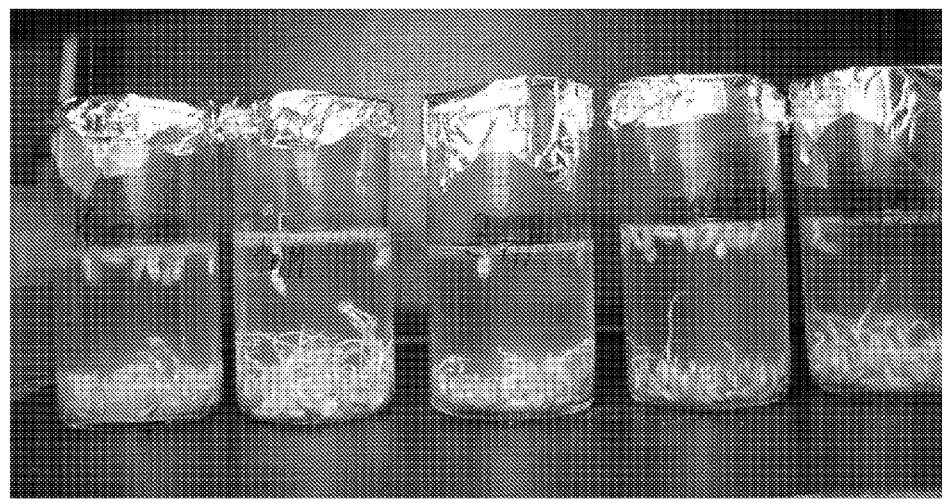
Fig. 7. SkQ1 at concentration of 1 nM dramatically enhances germination of rice seeds under water.

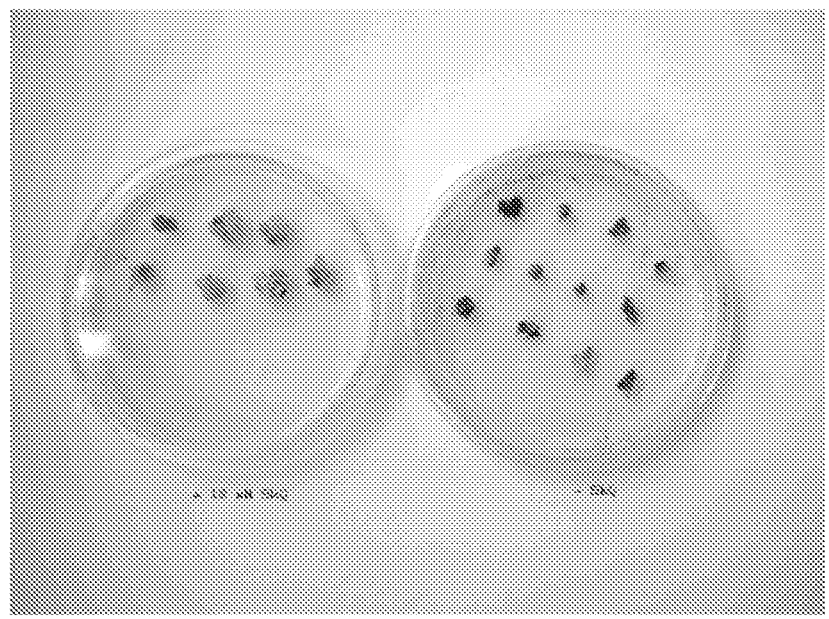
Fig. 8. SkQ1 enhances resistance of sugar cane calli to anaerobic stress.

COMPOSITION FOR REGENERATING AND STIMULATING GROWTH OF PLANTS AND FOR ADAPTING PLANTS TO DIFFERENT STRESS FACTORS

FIELD OF THE INVENTION

This invention relates to biotechnology. The invention can be used for stimulation of regeneration of plants from tissues and undifferentiated cells cultivated under artificial conditions. The present invention can also be applied in agriculture for acceleration of germination of seeds, increase in germination of aged, long-stored seeds as well as for increase of resistance of plants to biotic and abiotic stresses.

BACKGROUND

Regeneration of plants is obligatory and often limiting stage of such biotechnologies as cell selection, genetic engineering, somatic hybridization, generation of haploid and diploid plants, microclonal proliferation.

Microclonal proliferation is a method of vegetative proliferation of plants by activation of dormant buds, induction of formation of new (adventitious) buds or callus tissues with subsequent generation of plans from them. Apart from proliferation, this method also provides partial resistance of planting material to fungal, bacterial and virus diseases. To date all of elite planting material of potato, berry, vegetable and decorative cultures is produced by using microclonal proliferation. Clonal proliferation of lignosa is of especially great interest [Ahuja, M. R. and W. J. Libby (Eds.). 1993. Clonal Forestry I: Genetics and biotechnology, Clonal Forestry II: Conservation and application. Springer-Verlag. Berlin]. When plans are produced from cultivated tissues, the two basic problems arise: how to increase amount of regenerants produced and how to implant them. To solve the first problem, nutrient medium is supplemented with growth regulators possessing cytokinin activity. However, shoots formed are "overfed" with cytokinin and, therefore, they take roots badly. Offered programs of gradual exclusion of cytokinins, addition of different growth regulators with auxin action demand a lot of time and not always produce a positive result. Long-term cultivation of plant tissues in vitro can cause undesirable mutations. To increase efficiency of clonal proliferation, more sophisticated regulation of plant regeneration is required (Tree Physiol. 2000 August; 20(14):921-8; Curr Opin Biotechnol. 2000 June; 11(3):298-302; Methods Mol Biol. 1999; 111:127-34).

Generation of haploid plants is applied to fix heterosis effect in hybrids. Upon usual proliferation by seeds, the optimum combination of parental genomes quickly collapses and, therefore, heterosis is not preserved longer 1-2 generations. To fix hybrid genotypes, haploid plants are produced from pollen of best plants $F_2$ and then duplication of chromosomes is achieved. Dihaploid plants produced can blossom normally and produce seeds. Since chromosomes in pair are identical, properties of such hybrid remain constant upon proliferation. To produce haploids, anthers or isolated pollen grains at early stages of development are introduced into in vitro culture and somatic embryogenesis or callusogenesis is induced. Probability of haploid plant generation does not exceed 5-10% of a number of planted anthers and significantly depends on a genotype of initial plants. Usually albinism can often be observed among regenerants. Upon production of haploids, the main goal is reprogramming of pollen grains from normal development (germination) to somatic embryogenesis. In this case, exogenetic regulation by phytohormones is ineffective. Some signals changing synthesis or activity of endogenous growth regulators are necessary.

Somatic hybridization is a process of fusion of isolated protoplasts separated from plant cells. Somatic hybridization allows to overcome noncrossing barriers upon distant hybridization, enables to generate unique combinations of nuclear and plastomic genomes of parents. Method of somatic hybridization is based on fusion of protoplasts induced by different ways followed by regeneration of cell wall at special nutrient media, hybrid cell division and callus formation. Then callus is used for plant regeneration. The most simple stage of this method is isolation and fusion of protoplasts, it is more difficult to achieve hybrid cell division, and the most difficult stage is assumed to be regeneration of plants from calli formed.

Isolation of plant tissues and their cultivation under artificial conditions induce genetic variation, which can also be shown in plants generated from cultivated cells. This phenomenon named somaclonal variation can be used, along with induced mutagenesis, for increase of genetic variation of crops in agriculture. Using selective nutrient media, it is possible to select cells with the given attributes directly in in vitro culture-to produce plants. Cell selection is mainly applied to increase resistance of plants to diseases and pests, and also to such adverse environmental factors as drought, salting, extreme temperatures, flooding etc. The selective systems aimed at increasing both specific and nonspecific resistance have been developed.

The combination of traditional and cell selection methods has already allowed to produce improved forms and new varieties of tomatoes, sugar cane, rice, barley, potato, spinach, fodder grasses and some other kinds of plants possessing resistance to biotic and abiotic stresses and high productivity [Karp A. Somaclonal variation as a tool for crop improvement//Euphytica, 1995, v. 85, p. 295-302].

Genetic engineering offers novel opportunities for generation of new varieties. Crops in agriculture tolerant to insects-pests, herbicides, adverse climatic conditions have been produced by introduction of genes derived from bacteria or plants. Plants with increased content of protein and essential amino acids, improved oil quality etc have been generated [Ya. I. Bur'yanov. Advances in Plant Gene Engineering Biotechnology.//Russian journal of plant physiology (*Fiziologiya rastenii*)-1999—v. 46—No 6—p. 930-944]. Almost all methods of genetic transformation comprise stages of cultivation of tissues in vitro and regeneration of plants from transgenic cells.

Thus efficiency of application of all cell biotechnologies depends on a possibility to produce a plant from cultivated cells (Plant Cell Culture Protocols. Second edition. V. M. Loyola-Vargas and F. Vazquez-Flota (eds). Humana Press, Mexico, 2005, 416 pp.; Plant Tissue Culture. 100 years since Gottlieb Haberlandt. M. Laimer and W. Rucker (eds.). Springer, Wien N.Y., 2003, 260 pp.).

The basic obstacle in wide use of cell cultures in selection is low regeneration ability of many lines and varieties. For example, in cotton, variety Coker and its derivatives are highly capable for morphogenesis, whereas a majority of other varieties has lowered or zero regeneration potential (Theor Appl Genet. 2004 August; 109(3):472-9.). Production of regenerants in some leguminous plants including such important plant as soya is a serious problem (Planta. 2004 October; 219(6):1042-9). In grain cereals, only cell cultures produced from embryos are really capable for morphogenesis (Vasil V., Chin Yu. L., Vasil I. K. Histology of somatic embryogenesis in cultured immature embryos of maize (*Zea mays* L.)//Protoplasma, 1985, v. 127, p. 1-8). A possibility of plant regeneration strongly depends on genotype (J Exp Bot. 2005 July; 56(417):1913-22.). The majority of commercial corn hybrids is characterized by low morphogenetic potential (Phillips R. L., Somers D. A., Hiberd K. A. Cell/tissue culture and in vitro manipulation. In: Corn and Corn Improvement—Agronomy Monograph 18. (Sprague G. F., Duddley J. W. eds) Am. Soc. of Agronomy, Madison, Wis., 1988, p. 345-387).

It is important that regeneration of plants from undifferentiated tissues and cells is a key stage upon production of any genetically modified plants.

Choice of Explant Tissue

The abilities of different plant tissues to form morphogenetic callus in in vitro culture are distinctive. This feature is most pronounced in monocotyledons. Meristematic tissues: unripe germs, inflorescences, meristem in nodes of tillering and in bases of leaves are characterized by highest regeneration potential. Differentiated tissues of leaves or roots have low ability to callusogenesis. Therefore, if plants are to be produced from cultivated cells, it is necessary to produce callus from competent tissues (Phillips R. L., Somers D. A., Hiberd K. A. Cell/tissue culture and in vitro manipulation. In: Corn and Corn Improvement—Agronomy Monograph 18. (Sprague G. F., Duddley J. W. eds) Am. Soc. of Agronomy, Madison, Wis., 1988, p. 345-387).

Variations of Hormonal Content of Nutrient Medium

The basic way of switching cells from unorganized growth to differentiation is change in concentration and ratio of hormones. To regenerate many plant species, it is necessary to increase concentration of cytokinins in a medium (Adv Biochem Eng Biotechnol. 2001; 72:157-82.). Ratio and concentration of phytohormones in a nutrient medium optimum for morphogenesis are species- and even variety-specific; therefore a new morphogenesis conditions should be selected upon introduction of new varieties or species of plants. In some cases a probability of morphogenesis increases upon replacement of traditionally used natural and synthetic phytohormones with compounds of other chemical nature but possessing a hormonal activity. However upon screening of a large amount of varieties, different authors have shown that stimulation is also variety-specific, and in case of success frequency of plant regeneration has increased no more than 20% [Wilkinson, Thompson, 1987], [Ignatova et al., 1993; Dias S., Dolgikh Y. I. Role of physiological factors in increase of efficiency of plant regeneration from cultivated maize tissues. Biotechnology (in Russian), 1997, No 11-12, p. 32-36].

Ethylene clearly inhibits callus regeneration. Addition of ethylene precursors 1-aminocyclopropane-1-carboxylic acid or aminoethoxyvinylglycine to a nutrient medium for callus initiation caused significant reduction of frequency of embryogenic callus formation and decrease of a number of produced regenerants by 68% [Songstad D. D., Duncan D. R., Widholm J. M. Effect of 1-aminocyclopropane-1-carboxylic acid, silver nitrate and norbornadiene on plant regeneration from maize callus cultures//Plant Cell Rep., 1988, v. 7, p. 262-265.] [Vain P., Flament P., Soudain P. Role of ethylene in embryogenic callus initiation and regeneration in Zea mays L.//J. Plant Physiol., 1990, v. 135, p. 537-540]. Inclusion of compounds inhibiting physiological effect of ethylene-norbornadiene or silver nitrate, into the medium, on the contrary, stimulated embryogenic callus formation and raised regeneration efficiency in a majority of tested genotypes by 15-20% [Vain P., Flament P., Soudain P. Role of ethylene in embryogenic callus initiation and regeneration in Zea mays L.//J. Plant Physiol., 1990, v. 135, p. 537-540]. [Hoisington D. A., Bohorova N. E. Towards the production of transgenic tropical maize germplasm with enhanced insect resistance. In: Current issues in Plant Molecular and Cellular Biology (Terzi M., Cella R., Falavigna A. eds.), Kluwer Acad. Publishers., Netherlands, 1995, p. 327-221].

In some cases, addition of abscisic acid to the medium enhances morphogenesis. In wheat, addition of abscisic acid at micromolar concentration inhibited premature germination of isolated embryos and stimulated embryogenic callus formation [Brown C., Brooks F. J., Pearson D., Mathias R. J. Control of embryogenesis and organogenesis in immature wheat embryo callus using increased medium osmolarity and abscisic acid//J. Plant Physiol., 1989, v. 133, p. 727-733; Carman J. G. Improved somatic embryogenesis in wheat by partial simulaton of the in-ovulo oxygen, growth-regulators and desiccation environments//Plants, 1988, v. 175, p. 417-424; I. F. Shayakhmetov, F. M. Shakirova. Somatic Embryogenesis in Wheat Cell Suspension Cultures in the Presence of Abscisic Acid.//Russian journal of plant physiology (*Fiziologiya rastenii*), 1996, v. 43, p. 101-103]. In tissue culture of wild turnip (*Brassica napus*) and maize, effect of abscisic acid on regeneration of plants was positive for some varieties but negative for others [Raldugina G. N., Sobolkova G. I. Genotypic differences upon abscisic acid action on callus cultures *Brassica napus* L.//Russian journal of plant physiology (*Fiziologiya rastenii*), 1994, v. 41, p. 702-706; Yu. I. Dolgikh, T. N. Pustovoitova, N. E. Zhdanova. Hormonal regulation of somatic embryogenesis on maize. In Phytohormones in Plant Biotechnology and Agriculture, Proceedings of NATO-Russia Internation Workshop, Kluwer Academic Publishers, 2003, p. 243-247].

Rather often, none of the media used provide production of plants-regenerants [Armstrong C. L., Romero-Severson J., Hodges T. K. Improved tissue culture response of an elite maize inbred through backross breeding, and identification of chromosomal regions important for regeneration by RFLP analysis//Theor. Appl. Genet., 1992, v. 84, p. 755-762].

Inclusion of Individual Amino Acids into Medium Content

Amplification of morphogenetic potential has been observed in some cultures upon addition of some amino acids to medium. For instance, agrinine-containing media are used for wheat, proline-containing media are used for maize [Salmenkallio M, Sopanen T. Amino Acid and Peptide Uptake in the Scutella of Germinating Grains of Barley, Wheat, Rice, and Maize//Plant Physiol. 1989 v. 89 p. 1285-1291]. It was recommended to use proline at high concentrations for increase of frequency of formation of friable embryogenic callus with prolonged ability of regeneration [Duncan D. R., Williams M. E., Zehr B. E., Widholm J. M. The production of callus capable of plant regeneration from immature embryos of numerous *Zea mays* genotypes//Planta, 1985, v. 165, p. 322-332]. According to Rapela's data, inclusion of 400 mg/L proline into medium resulted in 2-3-fold increase of frequency of embryogenic callus formation and plant regeneration [Rapela M. A. Organogenesis and somatic embryogenesis in tissue culture of Argentine maize (*Zea mays* L.)//J. Plant Physiol., 1985, v. 121, p. 119-122]. In other work, 20 mM proline caused increase in a number of regenerants per explant from 2.8 up to 7.6 [Kamo K. K., Becwar M. R., Hodges T. K. Regeneration of *Zea mays* L. from embryogenic callus//Bot. Gaz., 1985, v. 146, p. 327-334]. The data on application of asparagine are ambiguous: along with stimulation of somatic embryogenesis in cultivated maize tissues [Lupotto E. In vitro culture of isolated somatic embryos of maize (*Zea mays* L.)//Maydica, 1986, v. 31, p. 193-201; Morocz S., Donn G., Nemeth J., Dudits D. An improved system to obtain fertile regenerants via maize protoplasts isolated from a highly embryogenic suspension culture// Theor. Appl. Genet., 1990, v. 80, p. 721-726] its oppression has also been observed [Kamo K. K., Becwar M. R., Hodges T. K. Regeneration of *Zea mays* L. from embryogenic callus// Bot. Gaz., 1985, v. 146, p. 327-334]. The mechanism of influence of proline or asparagine on ability of morphogenesis has not been described.

Influence of Oligosaccharides

Oligosaccharides are formed during disintegration of plant cell walls. For instance, xyloglucan pentasaccharide 1.5-2-fold enhanced morphogenesis in wheat tussue culture [Pavlova Z. N., Ash O. A., Vnuchkova V. A., Babakov A. V., Torgov V. I., Nechaev O. A., Usov A. I., Shibaev V. N. Biological Activity of a Synthetic Pentasaccharide Fragment of Xyloglucan//Plant Sci. 1992 V. 85. P. 131-134], and trimerous oligosaccharide promoted somatic embryogenesis in cotton [Yu. I. Dolgikh, E. Yu. Shaikina, A. I. Usov, V. N. Shibaev, V. V. Kuznetsov. The Trisaccharide Fragment of Xyloglucan as a Regulator of Plant Morphogenesis//*Doklady Akademii Nauk.* 1998. v. 360. p. 417-419].

Electrostimulation of Morphogenesis

Passing the weak (1-2 µA) constant electric current through calli was shown to stimulate shoot regeneration. 1 to current resulted in increase of tobacco callus weight by 70% and 5-fold increase of a number of shoots formed [Goldsworthy A. The electric compass of plants//New Sci., 1986, No 1, p. 22-23]. In wheat callus, two-fold amplification of rhizogenesis and shoot formation were shown whereas they were entirely absent in the control [Rathore K. S., Goldsworthy A. Electrical control of shoot regeneration in plant tissue culture//Bio/technology, 1985, v. 3, p. 1107-1109]. Stimulation of somatic embryogenesis in lucerne protoplast culture [Dijak M., Smith D. L., Wilson T. J., Brown D. C. W. Stimulation of direct embryogenesis from mesophyllprotoplasts of *Medicago sativa*//Plant Cell Rep., 1986, v. 5, p. 468-470], and activation of shoot formation in cabbage, poplar, maize [Wang X., Wang Q., Song M., Zheng E. Effect stimulation with weak electric currents on in vitro culture of cabbage// Acta Bot. Sinica, 1993, v. 35, Suppl., p. 66-70; Dutta R. Studies on the mechanism of electrically induces growth and differentiation in plants in vitro: the cytomorphological profile. Abstr. VIII Intern. Congr. "Plant Tissue and Cell Culture", Florence, Italy, 1994, p. 49; Kitlaev G. B., Dolgikh Yu. I., Butenko R. G. Physiological action of electric current on maize cell culture in vitro. Doklady Akademii Nauk, 1994, v. 335, No 3, p. 393-395] were also found out. Electric current-induced stimulation of plant regeneration is independent of plant variety or species though quantitative variations are possible. Application of said method of increase of frequency of plant regeneration is limited by necessity to have rather complex technique and small throughput.

BRIEF DESCRIPTION OF FIGURES

FIG. 1. SkQ1 stimulates shoot formation from undifferentiated tissue of sugar cane.

FIG. 2. Development of sugar cane shoots at regeneration medium after 10 nM SkQ1-induced shoot formation.

FIG. 3. A sugar cane plant produced from callus by 10 nM SkQ1-induced stimulation of regeneration.

FIG. 4. SkQ1 stimulates root formation from tobacco undifferentiated tissue.

FIG. 5. Effect of different SkQ1 concentrations on formation of shoots and roots from maize calli.

FIG. 6. Effect of SkQ1 on formation of embryogenic callus in lucerne.

FIG. 7. SkQ1 at concentration of 1 nM dramatically enhances germination of rice seeds under water.

FIG. 8. SkQ1 enhances resistance of sugar cane calli to anaerobic stress.

DESCRIPTION

The invention is based on the principle that biologically active compounds, being linked with a Skulachev-ion, can be specifically delivered to mitochondria at the expense of energy of electrochemical potential of hydrogen ions. Such an approach has allowed to multifold decrease the amount of biologically active compounds administered and to specifically affect mitochondria which are the key element in the most important intracellular processes. Thus the elaborated approach appeared to allow to dramatically decrease unfavorable side effects of the biologically active compound employed.

Thus, one of the aspects of the present invention is the way to affect a plant by biologically active compounds targetedly delivered to mitochondria at the expense of energy of electrochemical potential of hydrogen ions.

In general, such a compound can be described by the following structure (I):

(structure I)

including solvates, isomers, agrochemically or physiologically acceptable salts thereof, wherein A is an effector-antioxidant of structure:

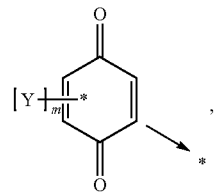

and/or reduced form thereof, wherein m is an integer from 1 to 3; each Y is independently selected from the group consisting of: lower alkyl, lower alkoxy; or two adjacent Y groups, together with carbon atoms to which they are attached to form the following structure:

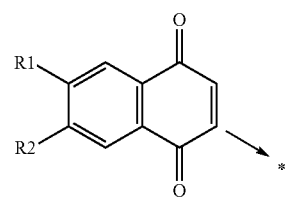

and/or reduced form thereof, wherein R1 and R2 may be the same or different and are each independently lower alkyl or lower alkoxy;

L is a linker group, comprising:

a) a straight or branched hydrocarbon chain optionally substituted with one or more substituents and optionally containing one or more double or triple bonds; or b) a natural isoprene chain;

n is an integer from 1 to 20;

B comprises:

a) a Skulachev-ion Sk:

where Sk is a lipophilic cation, Z is an acceptable anion; and/or b) a charged hydrophobic peptide containing 1-20 amino acid residues;

provided that in compound of structure (I) A is neither ubiquinone (e.g. 2-methyl-4,5-dimethoxy-3,6-dioxo-1,4-cyclohexadienyl) nor tocopherol or mimetic of superoxide dismutase or ebselen; when L is neither divalent decyl nor divalent pentyl or divalent propyl radical; and when B is triphenylphosphonium cation.

A further aspect of the present invention is the composition for targeted delivery of biologically active compound to mitochondria of a cell used for regeneration, stimulation of growth of plants comprising a compound of structure (I), wherein A—plastoquinone of structure:

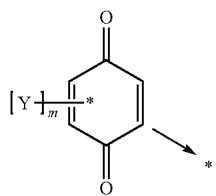

wherein Y is methyl, m=2;

L is a linker group, comprising:

a) a straight or branched hydrocarbon chain optionally substituted with one or more substituents and optionally containing one or more double or triple bonds; or b) a natural isoprene chain;

n is an integer from 1 to 20;

B comprises:

a) a Skulachev-ion Sk:

where Sk is a lipophilic cation, Z is an acceptable anion; and/or b) a charged hydrophobic peptide containing 1-20 amino acid residues;

provided that in compound of structure (I) A is neither ubiquinone (e.g. 2-methyl-4,5-dimethoxy-3,6-dioxo-1,4-cyclohexadienyl) nor tocopherol or mimetic of superoxide dismutase or ebselen; when L is neither divalent decyl nor divalent pentyl or divalent propyl radical; and when B is triphenylphosphonium cation;

including solvates, isomers, agrochemically or physiologically acceptable salts thereof.

A further aspect of the present invention is a composition useful for plants to overcome various stress factors comprising a compound of structure (I) -SkQ1:

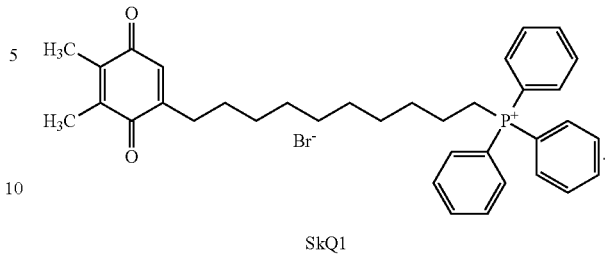

SkQ1

A further aspect of the present invention is a compound of structure (I) that can be used:

to stimulate regeneration of plants from tissues and undifferentiated cells cultivated under artificial conditions;

to accelerate germination of seeds;

to increase germination of aged, long-stored seeds;

to stimulate regeneration of plants from cuttings (rooting);

to increase flowering period;

to increase lifetime of cut flowers;

to increase biomass of plants and fruits;

to prevent fruit falling;

to enhance resistance of plants to pesticides;

to increase resistance of plants to biotic and abiotic stresses (salting, extreme temperatures, changes in light conditions), and also to enhance resistance to phytopathogens.

A further aspect of this invention is an agrochemically or physiologically acceptable composition to affect a plant or plant seeds comprising agrochemically or physiologically justified amount of a compound of Structure (I) and at least one agrochemically or physiologically acceptable diluent or filler. Agrochemically or physiologically acceptable diluent or filler may present a solvent, solid carrier or surfactant. In other words, agrochemically or physiologically acceptable composition of the present invention for affecting a plant or plant seeds can be used in the form of sprays, emulsive concentrates, suspended concentrates, concentrate solutions, spreading pastes, diluted emulsions, soluble powders, dispersive powders, moistened powders, dust, granules or as incapsulated in polymeric substance.

Examples of acceptable solvents are alcohols such as ethanol, propanol or butanol; glycols and their ethers or esters such as propylene glycol, dipropylene glycol ether, ethylen glycol or ethylen glycol monomethyl ether; ketones such as cyclohexanone, isophorone; water, nonepoxy or epoxy vegetable oils such as nonepoxy or epoxy turnip, castor, coconut or soybean oils.

Examples of acceptable solid carriers are natural minerals such as calcite, talc, kaolin, montmorillonite or attapulgite. Other granular inorganic or organic substances, for example, dolomite or grinded plant fragments can also be used.

Examples of acceptable surface-active compounds (surfactants) are nonionic, cationic and/or anionic surfactants depending on a type of active ingredient included in a composition.

A plant suitable to be affected by active ingredient or a composition of the present invention is any biological object related to plant kingdom according to the commonly accepted classification in biology.

A compound of Structure (I) can be applied both in itself and together with addition of natural and synthetic phytohormones (for example, 2,4-dichlorophenoxyacetic acid, cytokinins, abscisic acid, 3,6-dichloro-ortho-anisic acid, tricamba, chloramben etc.), compounds inhibiting physiological effect of ethylene (for example, norbornadiene, silver nitrate etc.), individual amino acids, oligosaccharides, and also with the subsequent electrostimulation or other physical exposure.

The following non-limiting Examples illustrate the preparation and use of the compounds of structure I but should not be understood as limiting the invention as modifications in materials and methods will be apparent to the skilled person. The following examples should not be construed as limiting the scope of this disclosure.

EXAMPLES

Examples of agrochemically acceptable compositions are given below in Tables:

1. Examples of Compositions in the Form of Solution for Stimulation of Plant Regeneration

TABLE 1.1

| Component | Role of component | Approximate amount |
|---|---|---|
| SkQ1 | Active compound | 1-50 µg |
| Water | Diluent | 1000 ml |

TABLE 1.2

| Component | Role of component | Approximate amount |
|---|---|---|
| SkQ1 | Active compound | 1-50 µg |
| Water | Diluent | 1000 ml |
| 10 mM sodium phosphate buffer, (pH 4.5-6.5) | Diluent | |

2. Examples of Compositions in the Form of Water-Soluble Granules for Stimulation of Plant Regeneration

TABLE 2.1

| Component | Role of component | Approximate amount |
|---|---|---|
| SkQ1 | Active compound | 45.6% |
| Lactose monohydrate | disaccharide | 50.6% |
| Polyvinylpyrrolidone | coupling compound | 0.8% |
| Co-polymers of ethylene oxide and propylene oxide | Surfactant | 3.0% |

TABLE 2.2

| Component | Role of component | Approximate amount |
|---|---|---|
| SkQ1 | Active compound | 45.6% |
| Lactose monohydrate | Disaccharide | 51.9% |
| Polyvinylpyrrolidone | coupling compound | 1.0% |
| Tween 20 | Surfactant | 1.5% |

3. An Example of a Spray for Stimulation of Plant Regeneration

TABLE 3

| Component | Role of component | Approximate amount |
|---|---|---|
| SkQ1 | Active compound | 0.1-1.0% |
| Vegeol SPO ™ | Surfactant | 0.01-1.0% |
| Tween 20 | Surfactant | 0.01-0.1% |
| Liquid vegetative wax jojoba | substance retarding penetration of a composition into a plant | 0.01-0.1% |
| Plastinol ™ | substance retarding penetration of a composition into a plant | 0.01-0.1% |
| Guar gum | substance preventing a composition from evaporation | 0.1-0.3% |
| Tixoseal ™ | substance forming a covering at particles | 0.01-0.05% |
| Difluoro-dichloromethane | compressed liquid | |

4. An Example of a Medium for Plant Regeneration

TABLE 4

| Component | Role of component | Approximate amount |
|---|---|---|
| SkQ1 | Active compound | 1-1000 nM |
| Agarized Murashige-Skoog medium | Medium | |
| Sucrose | Osmotic | 30 mg/L |
| 2,4-dichlorophenoxyacetic acid | phytohormone | 1 mg/L |

5. 1-50 nM SkQ1 included in media for hydroponics.

5. Production of Normal Sugar Cane Plants from Calli Induced by SkQ1 to Regeneration In this work, calli and explants of tobacco, sugar cane, maize, lucerne, potato and tomatoes were used. Calli were incubated at Petri dishes containing agarized Murashige-Skoog medium with 30 mg/L sucrose and 1 mg/L 2,4-dichlorophenoxyacetic acid. The cultivation was carried out at temperature 26° C., illumination intensity of 2 cd and the length of daylight of 16 hours. SkQ1 was added to autoclaved and cooled (up to 45° C.) nutrient medium immediately before callus planting. SkQ1 at concentrations of 0, 1.5, 5, 10, 20, 30 and 50 nM was used. Increase of callus green weight, a fraction of calli with shoots and roots and an average number of organs per a morphogenetic callus were taken into account after one month of cultivation.

6. SkQ1 Induces Regeneration from Calli of a Wide Range of Plants

Sugar Cane

SkQ1 at low concentration (10 nM) was found to induce formation of shoots from calli beginning with 19-th day of incubation (FIG. 1). Control calli did not reveal any features of shoot formation. At higher SkQ1 concentrations, though shoot formation was also observed but it occurred at later time (after 31-st day) and in lesser amount of calli.

When calli with shoots formed at 10 nM SkQ1-containing medium were transferred onto agarized regeneration medium, the formed shoots have continued to develop normally at the presence of 10 nM SkQ1 (FIG. 2). At the same time, development of shoots of calli transferred onto regeneration medium from medium without SkQ1 has been at the very initial stage.

The presence of higher SkQ1 concentrations in the regeneration medium was accompanied by termination of further development of shoots (100 nM SkQ1), or led to destruction of shoots (1000 nM SkQ1).

To produce normal plants, sugar cane shoots formed by 10 nM SkQ1 were transferred onto rootage agarized medium containing the same optimum SkQ1 concentration (10 nM). After root formation, the plants were transferred into water medium and then displanted into the ground. Estimation of the plant state was performed at every stage. It was shown that sugar cane shoots induced by 10 nM SkQ1 take roots properly and give normal viable plants (FIG. 3).

It is worthy of note that shoots formed at a medium supplemented with 100 nM or 1000 nM SkQ1 and further cultivated at a medium containing the same high SkQ1 concentrations appeared to be nonviable and died.

Tobacco

Effect of SkQ1 on callus formation (dedifferentiation) in tobacco leaf explants was investigated. Sterile leaf disks of plants *Nicotiana tabacum* cv Samsun were sliced with approximately 1 cm$^2$ size. The resulting explants were placed at standard MS medium for callus formation supplemented with phytohormones 0.5 mg/L 6-benzylaminopurine and 1 mg/L naphthylacetic acid. Test Petri plates were also supplemented with 0.6 µM SkQ1. Explants were cultivated in darkness for 5 weeks. During incubation callus was initially formed at wound explant surfaces. Then explants at test Petri dishes supplemented with SkQ1 revealed onset of secondary differentiation of callus tissues with root formation. Control Petri dishes without SkQ1 did not show any root formation (FIG. 4). In the course of a further incubation at test Petri dishes areas of differentiated explant tissues necrotized and died (it did not concern newly formed differentiated root tissues which did well), whereas control Petri dishes showed normal dedifferentiation of explant tissues.

Maize

Dose-dependent effect of SkQ1 on morphogenetic processes in maize callus was shown. At 1-10 nM SkQ1, increase of inoculum fraction that forms shoots and increase of an average number of shoots per callus were observed. No reliable increase in amount of rhizogenic calli was established but an average number of roots per callus increased significantly (FIG. 5). SkQ1 at 20 nM and higher concentrations inhibited morphogenesis, and the influence on shoot formation was more efficient than influence on rhizogenesis. Said compound did not affect essentially callus accretion. Variations in green weight resulted mainly from amount of formed roots. No reliable growth oppression induced by high SkQ1 concentrations was observed.

When callus cultivation was repeated using the same medium composition, the similar effect of SkQ1 was observed, with even more pronounced amplification of rhizogenesis.

Lucerne

Lucerne calli were cultivated for 1 month in the presence of different SkQ1 concentrations (0-10 nM). Effect of SkQ1 on callus growth (weight change) and regeneration ability (formation of calli with "green areas") were assessed. It was shown that SkQ1 does not affect significantly callus growth but 5 nM SkQ1 markedly (2.5-3-fold) stimulates regeneration. At higher SkQ1 concentrations, said positive effect eliminates (FIG. 6).

Potato and Tomato

Effect of SkQ1 on formation shoots and roots from leaf potato explants and stem tomato explants was investigated. Explants were incubated for 10 days in the presence of 10 nM SkQ1 or with no SkQ1. The data allow to conclude that SkQ1 significantly enhances formation of both shoots and roots in potato and tomato.

7. SkQ1 and Anaerobiosis of Plants

Germination of Rice Seeds Underwater

Effect of SkQ1 on germination of rice seeds under water (under anaerobic conditions) was studied. SkQ1 was added to water at concentrations of 0, 1, 3, 10, 30 nM. 1 nM SkQ1 was shown to enhance significantly germination of rice seeds (FIG. 7). SkQ1 at higher concentrations does not reveal such a stimulating effect.

Survival of Sugar Cane Calli After Anaerobic Stress

Effect of SkQ1 on survival of sugar cane calli following anaerobic stress was assessed. For this purpose, sugar cane calli were incubated for 48 hours under anoxic conditions and then were transferred under aerobic conditions at a nutrient medium containing 10 nM SkQ1 or no SkQ1 (control). In the presence of SkQ1, said calli were shown to possess markedly higher capability for survival and, besides, they retain capability for morphogenesis (FIG. 8).

The invention claimed is:

1. A method for stimulating regeneration, growth, and/or resistance to stress, or increasing the lifetime, of a plant, or cutting thereof, or its flower or fruit, comprising administering to the plant or portion thereof an effective amount of the compound of structure I:

(I)

or a solvate or isomer thereof, or an agrochemically or physiologically acceptable salt thereof, wherein:
A is an effector—antioxidant of structure:

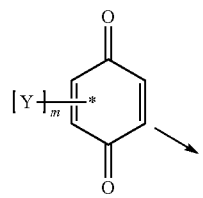

or reduced form thereof, wherein:

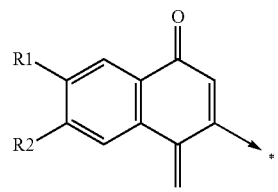

m is an integer from 1 to 3;
each Y is lower alkyl or lower alkoxy; or two adjacent Y groups, together with carbon atoms to which they are attached, form a following structure:

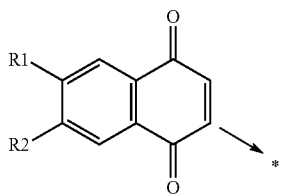

or reduced form thereof,
wherein R1 and R2 may be the same or different and are each independently lower alkyl or lower alkoxy;
L is a linker group, comprising:
  a) a straight or branched hydrocarbon chain which can be optionally substituted by one or more substituents and optionally contains one or more double or triple bonds; or
  b) a natural isoprene chain;
n is integer from 1 to 20;
B is a targeting group, comprising:
  $Sk^+Z^-$: wherein:
    Sk is a triphenylphosphonium cation; and
    Z is an acceptable anion;
provided that is not ubiquinone or tocopherol or mimetic of superoxide dismutase or ebselen; while L is divanlent decyl or divalent pentyl or divalent propyl radical; and
  an agrochemically or physiologically acceptable carrier thereof.

2. The method of claim 1, wherein Y of the composition is methyl and m=3.

3. The method of claim 1, wherein the composition stimulates regeneration of the plant from tissues and undifferentiated cells cultivated under artificial conditions.

4. The method of claim 1, wherein the composition is administered to a seed of the plant and accelerates germination of the seed.

5. The method of claim 1, wherein the composition is administered to an aged, long-stored seed of the plant and increases germination of the aged, long stored seed.

6. The method of claim 1, wherein the composition is administered for stimulating regeneration of a cutting from the plant.

7. The method of claim 1, wherein the composition increases a flowering period of the plant.

8. The method of claim 1, wherein the composition is administered to a flower from the plant, and increases the lifetime of a flower cut from the plant.

9. The method of claim 1, wherein the composition is administered to the plant or a fruit on the plant, and increases biomass of the plant or of the fruit.

10. The method of claim 1, wherein the composition is administered to a fruit on the plant, and prevents the fruit from falling from the plant.

11. The method of claim 1, wherein the composition enhances the plant's resistance to a pesticide.

12. The method of claim 1, wherein the composition enhances the plant's resistance to biotic and abiotic stresses.

13. The method of claim 1, wherein the composition enhances the plant's resistance to a phytopathogen.

* * * * *